United States Patent [19]

Tremulis

[11] Patent Number: 5,776,099
[45] Date of Patent: Jul. 7, 1998

[54] SINGLE LUMEN BALLOON CATHETER AND METHOD FOR ITS INTRALUMINAL INTRODUCTION

[75] Inventor: William S. Tremulis, Redwood City, Calif.

[73] Assignee: Micro Interventional Systems, Sunnyvale, Calif.

[21] Appl. No.: 816,007

[22] Filed: Mar. 10, 1997

Related U.S. Application Data

[63] Continuation of Ser. No. 415,002, Mar. 31, 1995, abandoned.

[51] Int. Cl.⁶ .................................................. A61M 29/00
[52] U.S. Cl. .............................. 604/96; 604/99; 606/194
[58] Field of Search ........................ 604/96, 99, 100, 604/101; 606/192, 194, 195

[56] References Cited

U.S. PATENT DOCUMENTS

| | | |
|---|---|---|
| 4,413,989 | 11/1983 | Schjeldahl et al. . |
| 4,813,934 | 3/1989 | Engelson et al. . |
| 5,201,754 | 4/1993 | Crittenden et al. ............ 606/194 |
| 5,209,728 | 5/1993 | Kraus et al. . |
| 5,246,420 | 9/1993 | Kraus et al. ..................... 604/95 |
| 5,304,198 | 4/1994 | Samson ........................... 606/194 |
| 5,312,340 | 5/1994 | Keith ................................. 604/96 |
| 5,318,529 | 6/1994 | Kontos ............................. 604/96 |
| 5,330,428 | 7/1994 | Wang et al. ..................... 604/96 |
| 5,348,537 | 9/1994 | Wiesner et al. .................. 604/96 |
| 5,364,347 | 11/1994 | Jang ................................. 604/53 |
| 5,364,354 | 11/1994 | Walker et al. ................... 604/96 |
| 5,378,237 | 1/1995 | Boussignac et al. ............ 604/96 |
| 5,380,282 | 1/1995 | Burns ............................... 604/96 |

Primary Examiner—Corrine M. McDermott
Attorney, Agent, or Firm—Townsend and Townsend and Crew LLP

[57] ABSTRACT

A balloon catheter has a combined balloon inflation and guide wire lumen. A guide wire tube in a distal port of the lumen inhibits loss of inflation medium through the port even when the balloon is inflated at relatively high pressures. The guide wire tube provides sufficient clearance with the guide wire, however, so that the catheter may be axially translated over the guide wire without excessive friction.

16 Claims, 2 Drawing Sheets

5,776,099

SINGLE LUMEN BALLOON CATHETER AND METHOD FOR ITS INTRALUMINAL INTRODUCTION

This is a continuation of application No. 08/415,002, filed Mar. 31, 1997, now abandoned, the disclosure of which is incorporated by reference.

BACKGROUND OF THE INVENTION

1. Field of the Invention

The present invention relates generally to the structure and use of medical catheters. More particularly, the present invention relates to the construction and use of a balloon catheter having at least one lumen capable both of receiving a movable guide wire and of supplying inflation medium to the balloon.

Balloon catheters are used for a variety of medical procedures including vessel dilatation, distal anchoring of a catheter, anchoring and positioning of guide catheters, and the like. Of particular interest to the present invention, balloon catheters are frequently introduced to a target location within a body lumen over a guide wire. The guide wire may be introduced percutaneously or through an open surgical incision and may then be advanced to a target site within the body lumen. The balloon catheter is then introduced over the guide wire until the balloon reaches the target site. After reaching the target site, the balloon can be used for a therapeutic purpose, e.g., dilatation of the body lumen, or as an anchor, positioning device, or the like. Heretofore, it has generally been necessary to provide separate lumens within the catheter for receiving the guide wire and for supplying inflation medium to the balloon.

The need to provide separate balloon inflation lumens and guide wire-receiving lumens is problematic in balloon catheters intended for introduction to very small body lumens, such as the coronary arteries and the vasculature of the brain. It will be appreciated that the need to provide two separate, parallel lumens necessarily increases the diameter or profile of the catheter, limiting the ability to introduce the catheter to the smallest blood vessels and other body lumens.

A number of balloon angioplasty designs have attempted to provide single or a common lumens for both balloon inflation and for receiving a guide wire. The problem with combining these two functions in a single lumen is that a seal must be provided in the distal guide wire exit port to prevent the loss of inflation medium when the balloon is inflated. This is a particular problem with balloon angioplasty catheters, where inflation occurs at very high pressures, typically above 8 atmospheres.

A number of attempts have been made to combine such functions, but none have been entirely successful. For example, U.S. Pat. No. 5,348,537 describes a hydrophilic sealing element within the distal end of a combination guide wire and balloon inflation lumen. While the seal formed will probably be adequate, the constriction of the seal about the guide wire exit port will add substantial friction, inhibiting repositioning of the catheter over the guide wire. U.S. Pat. No. 5,304,198, describes the use of a core wire to selectively open and close a valve at the distal end of a balloon catheter inflation lumen. Although the core wire can also act as a guide wire, the need to provide such a specialized guide wire limits the choice of movable guide wire to be employed in the system. Also, depending on the relative positions of the valve and wire, exchange of the wire or the catheter is impossible.

For these reasons, it would be desirable to provide improved balloon catheters having combined balloon inflation and guide wire-receiving lumens which overcome at least some of the deficiencies noted above. In particular, it would be desirable if such catheters and methods were usable with conventional, movable guide wires and permitted loading of the catheter over the proximal end of a guide wire which has been previously introduced to the target body lumen, such as a blood vessel. Such catheters and methods should permit relatively free movement of the catheter over the guide wire, typically presenting a friction force below about 0.5 g to the user, while inhibiting the loss of inflation medium when the balloon is inflated, typically to a volume under 2 cc/min when the balloon is inflated even at 10 atmospheres or above.

2. Description of the Background Art

U.S. Pat. No. 5,318,529, describes an angioplasty balloon catheter having a guide wire tube which receives a guide wire permanently received in an inflation lumen of the catheter. The guide tube has a very close tolerance over guide wire, preferably below 0.0005 inch and optionally filled with a thixotropic material or elastomeric seal to prevent blood seepage and loss of inflation medium. Friction between the guide tube and guide wire is relied on to transmit axial force to the balloon. U.S. Pat. No. 5,348,537, describes a balloon angioplasty catheter having a hydrophilic sealing element at a distal end of an inflation lumen, where swelling of the hydrophilic element prevents leakage of inflation medium past the seal. U.S. Pat. No. 5,304,198, describes a single-lumen balloon catheter having a valve seat at a distal end of the single lumen. A valve plug, e.g. in the form of a ball, is placed on a control wire to permit selective opening and sealing of the lumen, and the control wire may optionally terminate in a coil tip. Other patents disclosing balloon catheters having guide wire and inflation lumens in different combinations include U.S. Pat. Nos. 5,380,282; 5,378,237; 5,364,347; 5,330,428; 5,312,340; 5,246,420; and 5,201,754.

SUMMARY OF THE INVENTION

According to a method of the present invention, a balloon catheter is loaded over the proximal end of a guide wire so that a constant diameter portion of the guide wire is received in a catheter lumen having a distal guide wire port. The balloon catheter is axially translated over the constant diameter portion of the guide wire in order to position the balloon at a target location within a body lumen of a patient. After reaching the target location, the balloon is inflated with a liquid inflation medium through the catheter lumen. The guide wire port has a fixed diameter which is sufficiently large to permit relatively free movement of the catheter over the constant diameter portion of the guide wire but is sufficiently small to inhibit loss of inflation medium when the balloon is inflated, even at relatively high pressures. In particular, when the balloon is inflated to a pressure 10 atmospheres, the loss of liquid inflation medium will be below 2 cc/min, preferably being below 1 cc/min, and more preferably being below 0.1 cc/min. When axially translating the balloon catheter over the guide wire, the frictional force will preferably be below about 0.5 g.

A balloon catheter according to the present invention is intended for use in combination with a separate, movable guide wire of the type commonly used in medical procedures, particularly intravascular procedures, such as angioplasty. The balloon catheter includes a catheter body having a distal end, a proximal end, and an inflation lumen extending between said ends. A guide wire port is formed at the distal end of the inflation lumen, and a balloon is

3 mounted on the catheter body near the distal end. The balloon is connected to receive liquid inflation medium from the inflation lumen, and the guide wire port has a region with a fixed diameter selected to permit free movement of the catheter over a constant diameter portion of the separate guide wire while inhibiting loss of inflation media, even when the balloon is inflated at relatively high pressures. In a preferred embodiment, guide wire port includes a tube having an axial lumen for slidably receiving the guide wire. The tube has a length in the range from about 0.5 mm to 5 mm, and an axial lumen diameter in the range from 0.2 mm to 1 mm. The axial lumen of the tube will have a diameter selected to provide a clearance over the guide wire which results in a sliding force and leakage rate in the ranges set forth above. The annular clearance will usually be in the range from 0.003 mm to 0.02 mm. The tube will be composed of a lubricous polymer, typically selected from the group consisting of polyethylene, such as polytetrafluoroethylene, polyimide, and polyurethane. In the exemplary embodiment, the balloon catheter further comprises a coil support element extending through the balloon, typically connecting the distal tube to proximal portions of the catheter body. Usually, a hemostatic seal will be provided at the proximal end of the inflation lumen for sealing against the guide wire. Alternatively, a guide wire exit port may be provided in an intermediate region of the catheter body so that the catheter may be introduced over the guide wire in a "rapid exchange" or "monorail" manner. In the latter case, it will also be necessary to size the guide wire exit port (and optionally provide a tube therein) to inhibit loss of inflation medium without substantially impeding axial translation of the catheter over the guide wire.

DESCRIPTION OF THE SPECIFIC EMBODIMENTS

Figure 1:
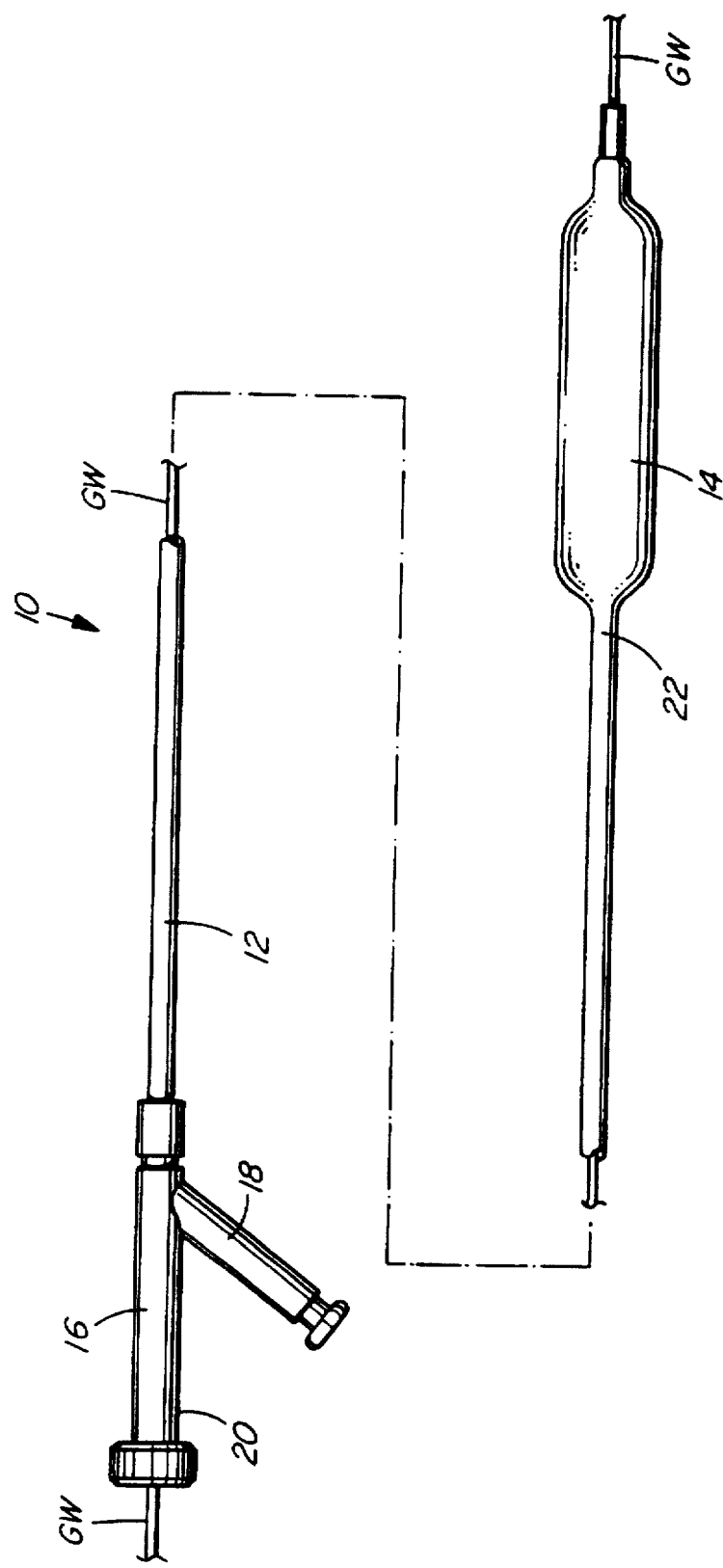
FIG. 1 is a side elevational view of a balloon catheter constructed in accordance with the principles of the present invention, shown introduced over a separate guide wire.

The present invention provides both a balloon catheter and a method for introducing the balloon catheter over a separate guide wire to a target site within a body lumen. The catheter will usually be a balloon angioplasty catheter, and the target site will usually be a region of stenosis within a patient's vasculature. It will be appreciated, however, that the design and method could be used with a variety of other medical catheters where the ability to combine the guide wire-receiving and balloon inflation functions in a single catheter lumen will be advantageous, particularly by reducing the diameter of the catheter at at least the distal end.

The balloon catheter of the present invention will comprise a catheter body having a proximal end and a distal end, and an inflatable balloon mounted near the distal end of the catheter body. The dimensions, materials, and construction of the catheter body may vary widely and will depend on the particular application intended for the catheter. In the case of angioplasty and other intravascular catheters, the catheter body will typically have the length in the range from 50 cm to 200 cm, usually in the range from 75 cm to 150 cm. The outside diameter of the catheter body will typically be in the range from 2 F (1 F (French) equals 0.33 mm) to 12 F, typically from 3 F to 10 F. The ability to combine the balloon inflation and guide wire-receiving functions in a single lumen makes the present invention particularly advantageous for small-diameter catheters, typically having a diameter from 2 F to 6 F over at least their distal ends. The catheter body will usually be formed by extrusion of an organic polymer, such as polyethylenes, polyvinylchlorides, polyurethanes, polyesters, polytetrafluorethylenes (PTFE), and the like. Optionally, the catheter body may be formed as a composite having a reinforcement material incorporated within the polymeric body in order to enhance its strength, flexibility, and toughness. Suitable enforcement layers include braiding, wire mesh layers, and the like. The catheter body will typically be formed with at least one continuous lumen extending from the proximal end to distal end being provided for both balloon inflation and guide wire-receiving functions, as described in greater detail below.

The balloon at or near the distal end of the catheter body may be formed separately or together with the body itself. For example, the balloon can be extruded and formed in a separate step, and joined thereafter to the distal end of the catheter body in a conventional manner, e.g. by heat fusing or adhesives. Alternatively, its possible to form the catheter body and inflatable balloon as a single extrusion, where the dimensions of the balloon are usually imparted by heat expansion and setting. In either case, the interior of the balloon will usually be open to the continuous lumen of the catheter body which serves as the inflation conduit.

A proximal hub will normally be provided at the proximal end of the catheter body. The hub will serve to provide access to the inflation/guide wire lumen, typically including at least two separate ports. A first port will be provided for connection to a balloon inflation source for providing pressurized, liquid inflation medium. A second port will be provided for introducing the guide wire, typically having a hemostatic valve or sealing element therein. The construction of such hubs and connection ports is conventional.

A guide wire tube will preferably be provided in the distal guide wire port of the catheter body lumen will have dimensions and will be composed of a material selected to provide a proper balance between friction against the movable guide wire when the catheter is being axially translated thereover and leakage of balloon inflation medium when the balloon is inflated. Preferably, the dimensions will be chosen to provide a sliding force against a conventional stainless steel guide wire below about 0.5 g, preferably below about 0.25 g. At the same time, the guide wire tube should inhibit leakage of inflation medium to below about 2 cc/min, preferably below about 0.1 cc/min, and more preferably being below 0.1 cc/min, even when the balloon is inflated up to about 10 atmospheres with a conventional aqueous-based balloon inflation medium, such as contrast media. Typically, the tube will have a length in the range from about 0.25 mm to 5 mm, preferably from 0.5 mm to 1 mm, and an axial lumen diameter in the range from 0.2 mm to 1 mm, typically from 0.25 mm to 0.5 mm. The most critical dimension, of course, is relative size of the axial lumen diameter to the outer diameter of the separate guide wire. Typically, the difference between these diameters will be in the range from 0.001 mm to 0.03 mm, preferably being in the range from about 0.003 mm to 0.02 mm. The guide wire tube will have a lubricous axial lumen surface, typically being composed from a lubricous material, such as polyethylene, polytetrafluoroethylene, polyimide, polyurethane, and the like.

Figure 2:
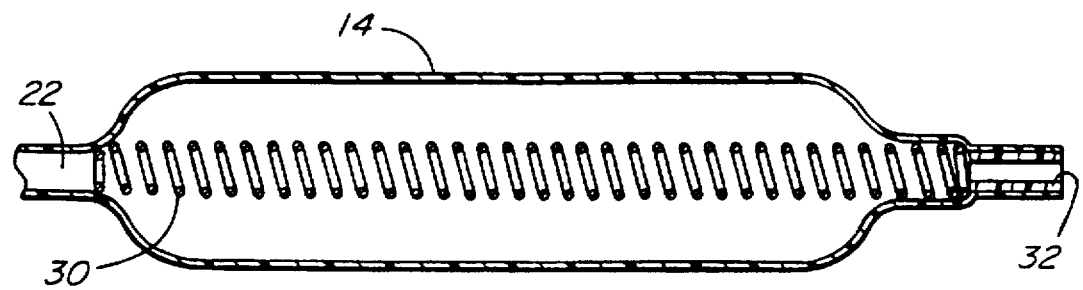
FIG. 2 is a detailed view of the distal end of the balloon catheter of FIG. 1, shown in section.
Figure 3:
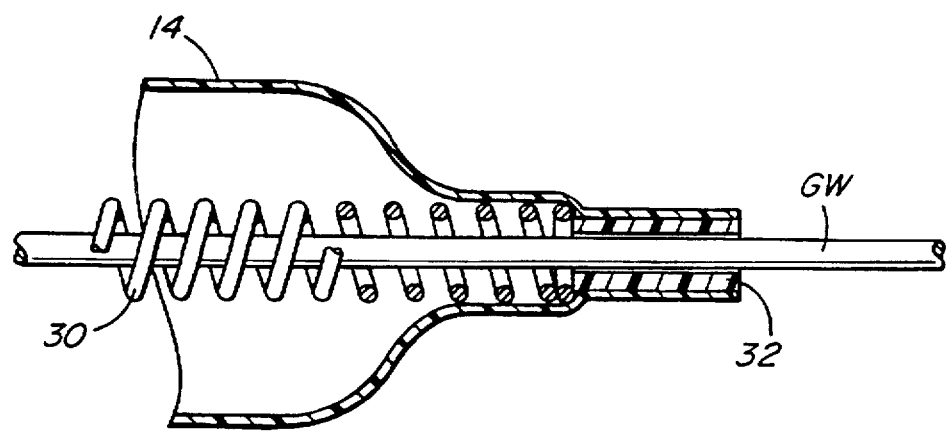
FIG. 3 is an even more detailed view of the distal tip of the catheter of FIG. 1, shown in section, over a separate guide wire.

Referring now to FIGS. 1–3, an angioplasty balloon catheter 10 comprises a catheter body 12 having an inflatable balloon 14 at its distal end and a proximal hub 16 at its proximal end. The hub includes a balloon inflation port 18 and a guide wire port 20, both of which communicate with an axial lumen 22 (FIG. 2) extending fully between the proximal hub 16 and the balloon 14.

Referring in particular to FIGS. 2 and 3, a support coil 30 extends from the distal end of lumen 22 to a guide wire tube 32 which is located distally of balloon 14. Support coil 30 provides mechanical support and column strength for the balloon region of the catheter. A guide wire GW is received through the guide wire tube 32, as best seen in FIG. 3. The guide wire tube is configured and constructed as described above in order to permit relatively free axial translation of the catheter 10 over the guide wire GW while substantially inhibiting the loss of balloon inflation medium contained within the balloon 14.

The balloon catheter 10 is introduced over the separate, movable guide wire GW in a conventional manner. Usually, the balloon catheter 10 will be loaded over the proximal end of the guide wire GW, after the guide wire has been positioned within the target body lumen. The balloon catheter 10 may then be advanced over the guide wire so that the balloon 14 also reaches the target location. During such introduction, of course, the balloon may be relatively easily axially translated over the guide wire to achieve the desired positioning. Once in place, the balloon is inflated with loss of inflation medium inhibited for the reasons described above.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A method for introducing a balloon catheter over a guide wire, said method comprising:
   providing a guide wire having a constant diameter over substantially the entire length of the guide wire, and a catheter body with an inflation lumen, a balloon and a guide wire port at a distal end of the inflation lumen, said guide wire port being dimensioned slightly larger than said constant diameter of said guide wire;
   loading the catheter body over a proximal end of the guide wire, wherein an annular clearance is established between the guide wire and the guide wire port;
   axially translating the catheter body over the guide wire to position the balloon at a target location within a body lumen of a patient;
   positioning the guide wire port of the catheter body over the guide wire;
   inflating the balloon of the catheter body with a liquid inflation medium through the inflation lumen, wherein the guide wire port permits free movement of the guide wire relative to the guide wire port and wherein the annular clearance has an area which concurrently permits minor leakage of said liquid inflation medium from said balloon through said annular clearance while substantially inhibiting loss of the inflation medium from said balloon through said annular clearance while the balloon is inflated.

2. A method as in claim 1, wherein the balloon is inflated to a pressure of 10 atmospheres and the loss of inflation medium is below 2 cc/min.

3. A method as in claim 1 or 2, wherein the catheter body may be axially translated over the guide wire with a force below about 50 g.

4. A method as in claim 1, wherein the catheter body is positioned within a blood vessel.

5. A method as in claim 1, further comprising moving the guide wire axially relative to the guide wire port after the balloon has been inflated without losing a substantial amount of inflation medium.

6. A balloon catheter for use in combination with a separate, removable guide wire, said balloon catheter comprising:
   a catheter body having a distal end, a proximal end, an inflation lumen extending between said ends, and a guide wire port at the distal end of the inflation lumen said guide wire port being dimensioned slightly larger than said guide wire; and
   a balloon near the distal end of the catheter body and connected to receive liquid inflation medium from the inflation lumen;
   wherein an annular clearance between said guide wire and the guide wire port permits substantially frictionless free movement of the catheter body over a constant diameter portion of the separate removable guide wire and wherein the annular clearance has an area which permits minor leakage of said liquid inflation medium from said balloon through said annular clearance while substantially inhibiting loss of inflation medium while the balloon is inflated.

7. A balloon catheter as in claim 6, wherein the guide wire port includes a tube having an axial lumen for slidably receiving the guide wire.

8. A balloon catheter as in claim 7, wherein the axial lumen has a diameter which provides an annular clearance over the guide wire in the rage from 0.001 mm to 0.03 mm.

9. A balloon catheter as in claim 7, wherein the tube has a length in the range from 0.25 mm to 5 mm and an axial lumen diameter in the range from about 0.2 mm to 1 mm.

10. A balloon catheter as in claim 9, wherein the tube is composed of a polymer selected from the group consisting of polyethylene, polytetrafluoroethylene, polyimide, and polyurethane.

11. A balloon catheter as in claim 6, further comprising a coil support element extending through the balloon.

12. A balloon catheter as in claim 6, further comprising a hemostatic seal at the proximal end of the inflation lumen for sealing against the guide wire.

13. A balloon catheter system comprising in combination:
   a balloon catheter comprising a catheter body having a distal end, a proximal end, an inflation lumen extending between said ends, and a guide wire port at the distal end of the inflation lumen, the balloon catheter further including a balloon near the distal end of the catheter body and connected to receive liquid inflation medium from the inflation lumen; and
   a movable guide wire having a constant diameter portion and a distal end portion, wherein the guide wire is apart from but receivable within the inflation lumen of the balloon catheter;
   wherein an annular clearance between the guide wire and the guide wire port permits free movement of the catheter body over a constant diameter portion of the separate removable guide wire and wherein the annular clearance has an area which permits minor leakage of inflation medium from said balloon through said annular clearance while substantially inhibiting loss of the inflation medium while the balloon is inflated, the distal end portion of the guide wire having a diameter slightly less than the fixed diameter of the guide wire port so that the distal end portion can be moved axially through the guide wire port.

14. A method for introducing a balloon catheter over a guide wire, said method comprising:

providing a catheter body with an inflation lumen, a balloon and a guide wire port at a distal end of the inflation lumen, and a guide wire having a constant diameter portion and a distal end portion said guide wire port being dimensioned slightly larger than said constant diameter portion of said guide wire port;

loading the catheter body over a proximal end of the guide wire, wherein an annular clearance is established between the guide wire and the guide wire port;

axially translating the catheter body over the guide wire to position the balloon at a target location within a body lumen of a patient;

inflating the balloon of the catheter body with a liquid inflation medium through the inflation lumen, wherein the guide wire port permits free movement of the constant diameter portion of the guide wire and wherein an annular clearance has an area which concurrently permits minor leakage of said liquid inflation medium from said balloon through said guide wire port while substantially inhibiting loss of inflation medium while the balloon is inflated; and moving the distal end portion of the guide wire through the guide wire port into the inflation lumen to allow the liquid inflation medium to pass through the guide wire port into the body lumen.

15. The method of claim 14 wherein the moving step is carried out by proximally withdrawing the distal end portion of the guide wire through the guide wire port.

16. The method of claim 14 wherein the moving step is carried out by axially translating the catheter body over the guide wire so that the guide wire port passes over the distal end portion of the guide wire.

* * * * *